(12) United States Patent
Fryan et al.

(10) Patent No.: US 6,337,080 B1
(45) Date of Patent: Jan. 8, 2002

(54) INSECT CONTROL MAT

(75) Inventors: Michael C. Fryan; James J. Olson, both of Racine, WI (US)

(73) Assignee: S. C. Johnson & Son, Inc., Racine, WI (US)

(*) Notice: Subject to any disclaimer, the term of this patent is extended or adjusted under 35 U.S.C. 154(b) by 0 days.

(21) Appl. No.: 09/468,532

(22) Filed: Dec. 21, 1999

(51) Int. Cl.[7] ................................................ A01N 25/32
(52) U.S. Cl. ....................... 424/409; 424/405; 424/406; 424/411; 424/10.4; 424/DIG. 10; 514/25; 514/136; 514/453; 514/456; 514/531; 514/555; 514/919
(58) Field of Search ................................ 424/405, 403, 424/406–409, 411, 40, 10.4, DIG. 10; 514/919, 531, 453, 136, 25, 555, 312, 456

(56) References Cited

U.S. PATENT DOCUMENTS

| | | | |
|---|---|---|---|
| 4,663,315 A | * | 5/1987 | Hasegawa et al. ............ 514/86 |
| 5,135,744 A | | 8/1992 | Alexander et al. ........ 424/78.17 |
| 5,469,968 A | | 11/1995 | Matthews et al. ........... 206/532 |
| 5,645,845 A | | 7/1997 | Neumann et al. ............ 424/405 |
| 5,968,540 A | | 10/1999 | Brenner et al. ............. 424/405 |

FOREIGN PATENT DOCUMENTS

EP    0 671 123 A1    3/1994

OTHER PUBLICATIONS

Davis et al., A Comparison Of the Aversiveness of Denatonium Saccharide and Quinine in Humans *Bulletin of the Psychonomic Society*, 1987, 25(6), 462–463.

Sales literature from Macfarlan Smith Ltd., Edinburgh, Scotland. Acknowledged prior art.

Product list from Atomergic Chemetals Corporation. Acknowledged prior art.

* cited by examiner

*Primary Examiner*—Neil S. Levy

(57) ABSTRACT

An insect control mat having a heatable substrate; an insect control active material; and an aversion material in an amount effective to cause a person to avoid retaining the mat in the person's mouth. A method of controlling insects by use of such a mat is also disclosed.

12 Claims, 1 Drawing Sheet

INSECT CONTROL MAT

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

The present invention relates to insect control and specifically to insect control mats, typically for use with heaters.

Insect control mats for use with heaters or moving air are well known in the art. The mats are typically made of absorbent, heat-resistive materials. They are treated with insect control active materials and are then placed on heaters of various sorts or in blower devices. The active ingredients are chosen to be such that an effective amount of insect control is achieved by release of the insect control active materials under the heat or moving air use conditions.

It is known that children, pets, and the like will sometimes chew or ingest non-food items. Insect control mats appear not to have caused toxicity problems around children or pets, perhaps because of relatively low concentrations of insect control active materials, the generally non-inviting appearance of the mats or the heaters, or for other reasons. However, new uses for mats, especially for outdoor insect control, have led to the introduction of mats having high amounts of active ingredients, amounts sufficiently high that a child or animal could suffer undesirable effects if such a mat were eaten. Furthermore, such mats are sometimes intend for use in attractive devices that are more likely to be placed on table tops and in other areas where a child's interest might be sparked.

It can therefore be seen that there is a newly important need for an improved insect control mat made to discourage children or animals from keeping the mat in their mouths.

BRIEF SUMMARY OF THE INVENTION

The following definitions apply throughout. An "aversion material" is a chemical or mixture of chemicals, whether synthetic or naturally occurring, that, when present in or on a substance in non-toxic amounts, will cause a person to avoid retaining the substance in the person's mouth. A "non-toxic amount" of a material is defined as an amount that can be held in a person's mouth and then expelled without a negative effect on the health of the person. A "bittering agent" is an aversion material that causes a repellingly bitter taste when placed in the mouth in non-toxic amounts. A "spicy repellent" is an aversion material other than a bittering agent that causes a repelling heat, spicy pain, or revolting taste when placed in the mouth in non-toxic amounts.

"Insect" means actual insects and also arthropods and other small animals commonly controlled by the same means used to control insects. An "insect control active material" is an insecticide, an insect repellent, or other material that causes modifications in insect behavior or development. An insect control active material is "volatile" if it evaporates in effective amounts under the intended conditions of use, the parameters of such conditions of use including but not limited to temperature and air flow. An "insect control mat" is a substrate of a selected material that bears or incorporates a volatile insect control material. Insect control mats are commonly available for use with heaters of various sorts and are impregnated with or otherwise contain or support an insect control material that is driven off by heat or moving air in amounts effective to repel or otherwise control flying insects. An amount of a material is an "effective amount" if it is sufficient to have the intended effect. An insect control material will be understood as being "toxic" if it causes undesirable symptoms in a person or domestic animal when consumed in the amount present in an insect control mat. "Undesirable symptoms" can include but are not limited to merely unpleasant sensations.

The invention provides an improved insect control mat that includes a heatable substrate, an insect control active material, and an aversion material in an amount effective to cause a person to avoid retaining the mat in the person's mouth. Preferably, the aversion material is selected from the group consisting of bittering agents, spicy repellents, and combinations thereof. More preferably, the aversion material is selected from the group consisting of denatonium benzoate, denatonium saccharide, denatonium chloride, sucrose benzoate, quinine, quinine hydrochloride, quinine sulfate, brucine, brucine sulfate, quassia, naringin, limonin, phenylthrocarbamide, quebracho, sucrose octaacetate, quassin, quercetin, berberine, and combinations thereof For reasons of cost and effectiveness, denatonium benzoate is the most preferred aversion material.

Many parents would prefer, if only to be very conservative, that their children not ingest insect control materials from insect mats, even in quantities that in fact will do no harm. Although the invention therefore is beneficial even with amounts of insect control active ingredient insufficient actually to be toxic to the average person, the invention is most beneficial when the insect control active ingredient is present in an amount sufficient to be toxic if ingested by a human or domestic animal. For example, the insect control active material d-allethrin (ISO-registered name), is commonly used in insect control mats in amounts of about 50 mg per mat, an amount that appears not to present practical toxicity problems. However, mats prepared for certain uses can contain at least 90 mg of d-allethrin. It is believed to be important that children be deterred from keeping such mats in their mouths.

The insect control active material present in the mat of the invention preferably is selected from the group consisting of d-allethrin, allethrin, prallethrin, bioallethrin, s-bioallethrin, esbiol, dichlorvos, transfluthrin, pyrethrum, and combinations thereof. The insect control active materials just referred to by their ISO registered names are further identified as follows:

TABLE 1

| ISO registered name | Commercial name or trademark |
| --- | --- |
| d-allethrin | Pynamin Forte ® (Sumitomo) |
| allethrin | Pynamin ® (Sumitomo) |
| prallethrin | Etoc |
| bioallethrin | |
| s-bioallethrin | Esbiothrin (available from AgrEvo Environmental Health, Inc.) |
| esbiol | |
| dichlorvos | DDVP |
| pyrethrum | natural chrysanthemum extracts |
| transfluthrin | |

All of these materials are of proven effectiveness against insects when used in insect control mats. Particularly preferred insect control active materials are d-allethrin, prallethrin, s-bioallethrin, allethrin, dichlorvos, and combinations thereof, and most preferred is d-allethrin in a total amount greater than or equal to 50 mg. For certain applications, d-allethrin in a total amount greater than or equal to 90 mg is preferred, with an amount greater than or equal to 250 mg being ideal, including amounts as high or higher than 600 mg. The higher amounts of d-allethrin are used in volatile dispensers in which the insect control mat is suspended above the flame of a candle, lamp, or the like, within the chimney of a hurricane lamp-type of device. Preferably the mat is held with an edge of the mat presented toward the flame so that hot gases flow over opposite sides of the mat.

In a preferred embodiment, the heatable substrate of the insect control mat is made of a material selected from the group consisting of matted fibrous materials, ceramic materials, a contained gel, and a polymeric material. When matted fibrous materials are used, a preferred material includes matted cellulosic materials.

In an alternative embodiment, the heatable substrate is a gel that contains the insect control material, the gel being contained within a heat-resistant cup, preferably a cup made of metal or heat-resistant plastic. The gel can be contained within the cup by a volatile-permeable membrane. See e.g. U.S. Pat. No. 5,645,845 for an example of gel-based systems. (The disclosure of this patent and all patents and publications cited herein are incorporated herein by reference as if fully set forth.) A silica gel is preferred, such as that commercially available under the trade name Cabosil.

Alternatively, the heatable substrate can be a polymeric material impregnated with the insect control material. Examples of such polymeric materials are disclosed in European Patent Application No. 94830104.91 (Publication number 0 671 123 A1). Preferred is the block co-polymer comprising an elastomeric polymer and a stiff polymer, such as a polyether-polyamide co-polymer, as disclosed therein The method of the invention for controlling insects includes the following steps. First, an insect control mat is provided that has a heatable substrate; an insect control active material; and an aversion material in an amount effective to cause a person to avoid retaining the mat in the person's mouth. Then, the insect control mat is exposed to heat sufficient to release an amount of the insect control material effective to control insects.

DETAILED DESCRIPTION OF THE INVENTION

Figure 1:
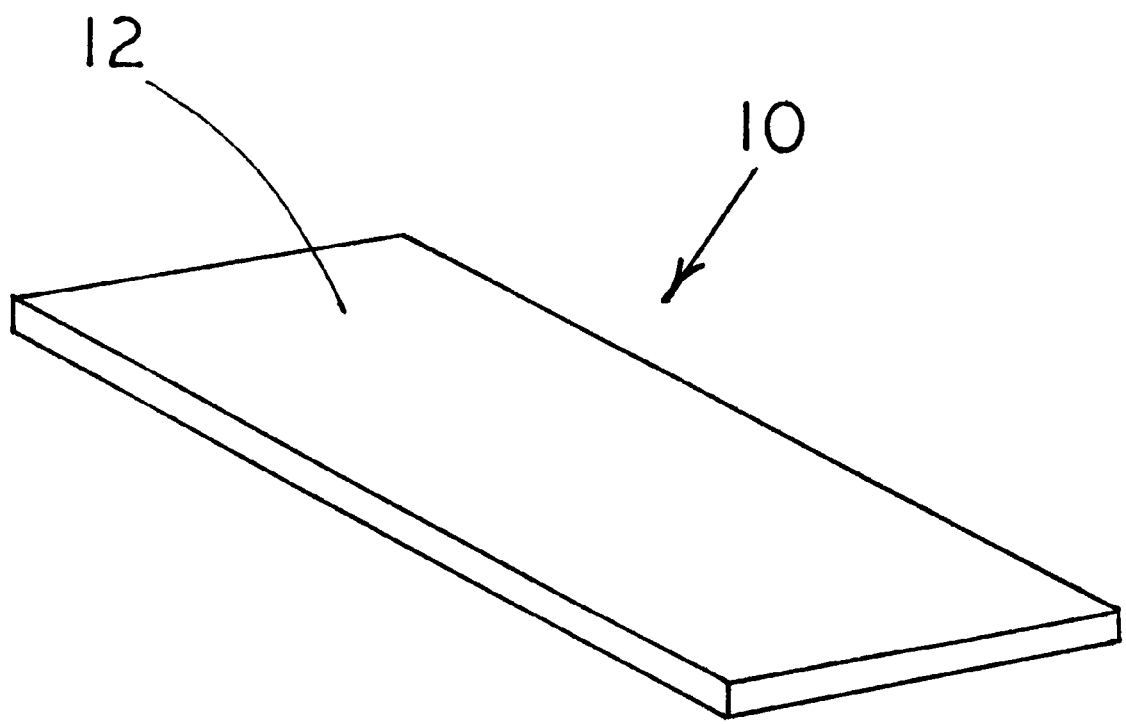
FIG. 1 is an insect control mat of a shape commonly commercially available for use with heater devices.

Turning now to the drawing, an insect control mat of a shape commonly commercially available is shown generally at 10 in FIG. 1. The typical mat 10 shown is generally flat and rectangular with atypical thickness on the order of 0.5 to 6 mm, with a thickness of 0.9 to 3 mm being more common. However, curved, cylindrical, fan-folded, and many other geometries are also possible (not shown). The invention is not limited to any particular mat geometry. Mat 10 has an upper side 12 and an under side (not shown).

The mat 10 is most commonly made of a matted or felted cellulosic material. Cotton, fiberglass, and other alternative, matted fibrous materials are also possible, as are porous ceramic materials, contained gels, and polymeric materials. All of these materials are examples of heatable substrates capable of supporting an insect control material to be dispensed. The invention is not limited to just the exemplary materials listed.

The mat 10 is impregnated, coated, or otherwise loaded with an insect control material. The insect control material thus can either permeate the mat 10 or reside on the surface of either the upper or under side. The insect control material is present in an amount such that, when the mat 10 is exposed to the desired amount of heat, an amount of the insect control material is released that is effective to control insects. The mat 10 also is impregnated, coated, or otherwise loaded with an aversion material in an amount effective to cause a person to avoid retaining the mat in the person's mouth. Such insect control and aversion materials can be loaded onto the mat 10 by being sprayed in liquid form, being deposited as a dose of liquid applied to the mat, or being applied by dipping, wet roller, or any other of the conventional ways to treat such mats. Dose deposition in the center of the mat, followed by the wicking of the dose throughout the mat, is preferred.

Examples of insect control mats made in accordance with the invention are as follows. The chemical ingredients listed are combined to form a liquid preparation and then are loaded on the mat in liquid form, preferably by dose deposition in the center of the mat. Then the mat is promptly enclosed within a sealed envelope or other container, whereupon the liquid is allowed to wick throughout the mat.

In the formulations, below, "yoshinox" is a common anti-oxidant (2,2'-methylene bis (6-tert-butyl-4-ethylphenyl)); and Isopar M is a hydrocarbon solvent sold by Exxon Chemical Company. Isopar M and ethanol function as solvents in each example. Isopropyl myristate is a solubilizer. CI Solvent Blue 35 is an optional, inert colorant. Amounts are in weight percents.

EXAMPLE 1

(Preferred Embodiment)

| Ingredient | (% w/w) |
|---|---|
| d-cis/trans allethrin (technical grade) | 23.75 |
| Yoshinox | 2.73 |
| CI Solvent Blue 35 | 0.13 |
| Isopropyl myristate | 0.17 |
| Isopar M | 9.08 |
| Ethanol | 1.16 |
| Denatonium Berizoate | 0.50 |
| Cellulose mat | 62.49 |
| Total | 100.00 |

EXAMPLE 2

(Hypothetical)

| Ingredient | (% w/w) |
|---|---|
| Allethrin | 30.97 |
| Yoshinox | 1.29 |
| CI Solvent Blue 35 | 0.06 |
| Isopropyl myristate | 0.08 |
| Isopar M | 4.30 |
| Ethanol | 0.61 |

-continued

| Ingredient | (% w/w) |
|---|---|
| Denatonium Saccharide | 0.18 |
| Cellulose mat | 62.50 |
| Total | 100.00 |

EXAMPLE 3
(Hypothetical)

| Ingredient | (% w/w) |
|---|---|
| Prallethrin | 11.65 |
| Yoshinox | 3.76 |
| CI Solvent Blue 35 | 0.18 |
| Isopropyl myristate | 0.23 |
| Isopar M | 12.51 |
| Ethanol | 7.06 |
| Denatonium Chloride | 2.12 |
| Cellulose mat | 62.5 |
| Total | 100 |

EXAMPLE 4
(Hypothetical)

| Ingredient | (% w/w) |
|---|---|
| s-bioallethrin | 6.63 |
| Yoshinox | 1.07 |
| CI Solvent Blue 35 | 0.05 |
| Isopropyl myristate | 0.07 |
| Isopar M | 3.56 |
| Ethanol | 20.09 |
| Quinine (or Quinine Hydrochloride or Quinine Sulfate) | 6.03 |
| Cellulose mat | 62.50 |
| Total | 100.00 |

EXAMPLE 5
(Hypothetical)

| Ingredient | (% w/w) |
|---|---|
| Prallethrin | 23.89 |
| Yoshinox | 0.42 |
| CI Solvent Blue 35 | 0.02 |
| Isopropyl myristate | 0.03 |
| Isopar M | 7.96 |
| Ethanol | 3.98 |
| Brucine (or Brucine Sulfate) | 1.19 |
| Cellulose mat | 62.5 |
| Total | 100 |

EXAMPLE 6
(Hypothetical)

| Ingredient | (% w/w) |
|---|---|
| Prallethrin | 6.92 |
| Yoshinox | 0.74 |
| CI Solvent Blue 35 | 0.04 |
| Isopropyl myristate | 0.05 |
| Isopar M | 2.48 |
| Ethanol | 20.98 |
| Naringin | 6.29 |
| Cellulose mat | 62.5 |
| Total | 100 |

EXAMPLE 7
(Hypothetical)

| Ingredient | (% w/w) |
|---|---|
| Prallethrin | 2.93 |
| Yoshinox | 2.08 |
| CI Solvent Blue 35 | 0.10 |
| Isopropyl myristate | 0.13 |
| Isopar M | 6.91 |
| Ethanol | 19.50 |
| Sucrose Benzoate | 5.85 |
| Cellulose mat | 62.5 |
| Total | 100 |

EXAMPLE 8
(Hypothetical)

| Ingredient | (% w/w) |
|---|---|
| Prallethrin | 2.50 |
| Yoshinox | 1.78 |
| CI Solvent Blue 35 | 0.09 |
| Isopropyl myristate | 0.11 |
| Isopar M | 5.91 |
| Ethanol | 20.86 |
| Sucrose Octaacetate | 6.26 |
| Cellulose mat | 62.5 |
| Total | 100 |

EXAMPLE 9
(Hypothetical)

| Ingredient | (% w/w) |
|---|---|
| Prallethrin | 12.30 |
| Yoshinox | 0.87 |
| CI Solvent Blue 35 | 0.04 |
| Isopropyl myristate | 0.05 |
| Isopar M | 2.91 |
| Ethanol | 16.40 |
| Quassin | 4.92 |
| Cellulose mat | 62.5 |
| Total | 100 |

EXAMPLE 10
(Hypothetical)

| Ingredient | (% w/w) |
|---|---|
| Prallethrin | 9.58 |
| Yoshinox | 0.68 |
| CI Solvent Blue 35 | 0.03 |
| Isopropyl myristate | 0.04 |
| Isopar M | 2.26 |
| Ethanol | 19.16 |
| Quercetin | 5.75 |
| Cellulose mat | 62.5 |
| Total | 100 |

EXAMPLE 11
(Hypothetical)

| Ingredient | (% w/w) |
|---|---|
| Prallethrin | 12.30 |
| Yoshinox | 0.87 |
| CI Solvent Blue 35 | 0.04 |
| Isopropyl myristate | 0.05 |
| Isopar M | 2.91 |
| Ethanol | 16.40 |
| Berberine | 4.92 |
| Cellulose mat | 62.5 |
| Total | 100 |

The preceding description is merely of preferred embodiments of the invention. One skilled in the art will readily apprehend alternative embodiments that nevertheless fall within the scope and breadth of the invention. Thus, the claims should be looked to in order to understand the full scope of the invention.

Industrial Applicability

An insect control mat has been disclosed effective for use with a heater for the control of insects and treated to discourage ingestion by pets or misuse by children or other persons.

What is claimed is:

1. A device for dispensing an insect control active, the device comprising a flame source, and an insect control mat suspended above the flame source, the mat comprising:
   a. a heatable substrate;
   b. an insect control active material; and
   c. an aversion material in an amount effective to cause a person to avoid retaining the mat in the person's mouth;
   wherein the aversion material is selected from the group consisting of denatonium benzoate, denatonium saccharide, denatonium chloride, sucrose benzoate, quinine, quinine hydrochloride, quinine sulfate, brucine, brucine sulfate, quassia, naringin, limonin, phenylthrocarbamide, quebracho, sucrose octaacetate, quassin, quercetin, berberine, and combinations thereof.

2. A method of controlling insects comprising the steps of:
   a. providing a device of claim 1; and
   b. exposing the insect control mat to the flame so as to provide heat sufficient to release an amount of insect control material effective to control insects.

3. The device of claim 1 wherein the heatable substrate is made of a material selected from the group consisting of matted fibrous materials, ceramic materials, a gel, and a polymeric material.

4. The device of claim 1 wherein the insect control active ingredient is present in an amount sufficient to be toxic if ingested by a human or a domestic animal.

5. The device of claim 1 wherein the insect control active material is selected from the group consisting of d-allethrin, prallethrin, s-bioallethrin, allethrin, diclorvos, transfluthrin, pyrethrum, and combinations thereof.

6. The device of claim 5 wherein the insect control active is selected from the group consisting of d-allethrin, prallethrin, s-bioallethrin, allethrin, and combinations thereof.

7. The device of claim 6 wherein the insect control active is d-allethrin in a total amount greater than or equal to 50 mg.

8. The device of claim 6 wherein the insect control active is d-allethrin in a total amount greater than or equal to 90 mg.

9. The device of claim 6 wherein the insect control active is d-allethrin in a total amount greater than or equal to 250 mg.

10. The device of claim 3 wherein the matted fibrous materials include matted cellulosic materials.

11. The device of claim 3 wherein the gel is a silica gel.

12. An insect control mat, comprising:
    a. a heatable substrate;
    b. an insect control active material; and
    c. an aversion material in an amount effective to cause a person to avoid retaining the mat in the person's mouth;
    wherein the aversion material is selected from the group consisting of denatonium benzoate, denatonium saccharide, denatonium chloride, sucrose benzoate, quinine, quinine hydrochloride, quinine sulfate, brucine, brucine sulfate, quassia, naringin, limonin, phenylthrocarbamide, quebracho, sucrose octaacetate, quassin, quercetin, berberine, and combinations thereof; and
    wherein the mat is suitable to be suspended above the flame of the claim 1 device.

* * * * *